United States Patent [19]

Keohane

[11] Patent Number: 5,446,053
[45] Date of Patent: Aug. 29, 1995

[54] METHODS OF INHIBITING DYSFUNCTIONAL UTERINE BLEEDING

[75] Inventor: Patrick Keohane, Indianapolis, Ind.

[73] Assignee: Eli Lilly and Company, Indianapolis, Ind.

[21] Appl. No.: 171,391

[22] Filed: Dec. 21, 1993

[51] Int. Cl.⁶ .................... A61K 31/445; A61K 31/40
[52] U.S. Cl. ..................................... 514/324; 514/408
[58] Field of Search ....................... 514/320, 324, 408

[56] References Cited

U.S. PATENT DOCUMENTS

| | | | |
|---|---|---|---|
| 4,133,814 | 1/1979 | Jones et al. | 260/326.55 |
| 4,380,635 | 4/1983 | Peters | 546/202 |
| 4,418,068 | 11/1983 | Jones | 424/267 |
| 5,075,321 | 12/1991 | Schreiber | 424/267 |

FOREIGN PATENT DOCUMENTS

WO93/10113 5/1993 WIPO.
WO93/1074 6/1993 WIPO.

OTHER PUBLICATIONS

Gottardis et al., Contrasting Action of Tamoxifen on Endometrial and Breast Tumor Growth in the Anthymic Mouse, *Cancer Research 48*, 8112–8115, Feb. 15, 1988.

Gottardis et al., Effect of Steroidal and Non–Steroidal Antiestrogens on the Growth of a Tamoxifen Stimulated Human Endometrial Carcinoma (Enca 101) in Athymic Mice, *Cancer Research*, 50, 3189–3192, Jun. 1, 1991.

Draper et al., "Effects of Raloxifene (LY139481 HCl) on Biochemical Markers of Bone and Lipid Metabolism i Healthy Postmenopausal Women", Hong Kong, Fourth Int'l Symp. on Osteoporosis, Mar. 29, 1993.

Bryant et al., "Protection from Bone Loss and Lowering of Serum Cholesterol in the Absence of Uterine Stimulation in Ovariectomized Rats", Am Soc. Bone & Min. Res., Tampa, Sep. 18–22, 1993.

Bryant et al., "Raloxifene is a Tissue Specific Estrogen Agonist", Am Soc. Bone & Min. Res., Tampa, Sep. 18–22, 1993.

Frolick et al., "In Vivo and In Vitro Metabolism of Raloxifene", Am. Soc. Bone & Min. Res., Tampa, Sep. 18–22, 1993.

Glasebrook et al., "Multiple Binding Sites for the Anti-estrogen Raloxifene", Am Soc. Bone & Min. Res., Tampa, Sep. 18–22, 1993.

Hock et al., "Combination of Raloxifene and Human Parathyoid Hormone 1–34; Increased Femur Bone Mass in Young Ovariectomized (OVX) Rats", Am. Soc. Bone & Min. Res., Tampa, Sep. 18–22, 1993.

Sato et al., "DEXA Analysis of Raloxifene Effects on the Bones From Ovariectomized Rats", Am. Soc. for Bone and Min. Res., Tampa, Sep. 18–22, 1993.

(List continued on next page.)

Primary Examiner—Zohreh Fay
Attorney, Agent, or Firm—James J. Sales; Gerald V. Dahling

[57] ABSTRACT

A method of inhibiting dysfunctional uterine bleeding comprising administering to a human in need thereof an effective amount of a compound having the formula

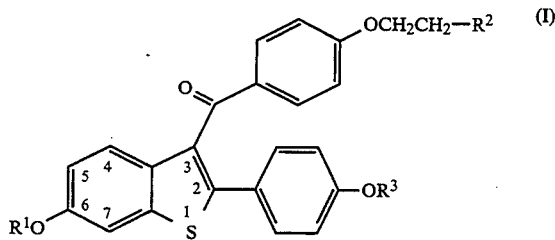

wherein
$R^1$ and $R^3$ are independently hydrogen,

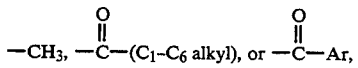

$-CH_3$, $-\overset{O}{\underset{\|}{C}}-(C_1-C_6\text{ alkyl})$, or $-\overset{O}{\underset{\|}{C}}-Ar$, wherein Ar is optionally substituted phenyl;
$R^2$ is selected from the group consisting of pyrrolidine, hexamethylenemino, and piperidino; or a pharmaceutically acceptable salt of solvate thereof.

3 Claims, No Drawings

OTHER PUBLICATIONS

Yang et al., "Raloxifene an Anti-Estrogen, Simulates the Effects of Estrogen in Inhibiting Bone Resorption Through Regulating TGFB-3 Expression in Bone;"-'.Am Soc. for Bone and Min. Res., Tampa, Sep. 18–22, 1993.

Black et al., "Distinct, Structure-Related Profiles of Estrogenic and Anti-Estrogenic Activity in the Tamoxifen and LY117018 Series;" The Endocrine Society, Abstract 1982.

Black et al., "Uterine Bioassay of Tamoxifen, Trioxifene, and New Estrogen Antagonist (LY117018) in Rats and Mice," Life Sciences, 26:1980, 1453–1458.

Black et al., "Differential Interaction of Antiestrogens with Cytosol Estrogen Receptors," Molecular and Cellular Endocrinology, 22:1981, 95–103.

Black et al., "Evidence for Biological Action of the Antiestrogens LY117018 and Tamoxifen by Different Mechanisms," Endocrinology 109; 1981, 987–989.

Black, L. J. "Biological Actions and Binding Properites of a New Estrogen Antagonsist LY117018," In: Homone Antagonists, 129–82, 1982 (M. K. Agarwal ed.) Walter de Gruyter and Co., Berlin New York.

Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5–6, 1982.

Black et al., The Antiestrogenic Action of LY139481: Species Uniformity Duration of Action and Kinetics of 3H-LY139481 Distribution In Vivo. Sixty-fifth Annual Meeting of the Endocrine Society, San Antonio, Texas, Jun. 8–10, 1983, abs. 93.

Black et al., Antagonism of Estrogen Action with a New benzothiophene Derived Antiestrogen, Life Sciences, 32:1983. 1031–1036.

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4-Dihydro-2(4-methoxyphenyl)-1-napthalenyl] [4-[2-pyrrolidinyl) ethoxyl]-phenyl] methanone, methanesulfonic acid salt, Journal of Medicinal Chemistry 22; 1979, 962–966.

Black et al., Antiestrogens 2. Structure Activity Studies in a Series of 3-Aroyl-2-arylbenzo[b]thiophene Derivatives Leading to [6-Hydroxy-2-(4-hydroxyphenyl)-benzo[b]thien-3-yl][4-[2-(1-piperidinyl)ethoxy]--phenyl]methanone Hydrochloride (LY156758), a Remarkably Effective Estrogen Antagonist with Only Minimal Intrinsic Estrogenicity, J. Med. Chem. 27(8), 1984, 1057–1066.

METHODS OF INHIBITING DYSFUNCTIONAL UTERINE BLEEDING

BACKGROUND OF THE INVENTION

Dysfunctional uterine bleeding is a common clinical problem in gynecology. Any woman may be affected during reproductive and later years. Dysfunctional bleeding is characterized by menorrhagia (excessive cyclical bleeding, greater than or equal to 80 ml/cycle) (Gleesen et al., *Eur J Obstet Gynecol Reprod Biol*, 48(3), 207–214 (1993)), metrorrhagia (abnormal frequency of cycles), bleeding in addition to normal cycles, or bleeding without normal cycles.

Potential causes of abnormal bleeding are numerous, and include physiological transition (e.g. menopause), pregnancy, endometrial cancer, or fibromyomata, and thus the diagnosis of dysfunctional uterine bleeding must be made after careful investigation to exclude these other causes (Galle et al., *Postgrad Med*, 93(2), 73–76 (1993)).

In most cases, dysfunctional uterine bleeding is associated with anovulation (Bayer et al., *JAMA*, 269(14), 1823–1828 (1993)). Anovulatory bleeding is frequent in pubertal and perimenopausal phases, and is physiological, probably related to changing estrogen levels (Id.). However, bleeding may be caused by chronic anovulation secondary to unopposed estrogen secretion which causes endometrial proliferation, and is associated with increased risk of endometrial cancer (Id.). Inappropriate estrogen levels, either excess estrogen or estrogen unopposed by appropriate progestagen (progesterone) levels, are considered the likely cause of many cases of dysfunctional uterine bleeding.

Treatment of anovulatory bleeding is designed generally to reduce bleeding, and more particularly to halt acute bleeding, prevent recurrence of bleeding, and prevent long-term complications (Id.). First treatment approaches are medical, and the areas and limitations of options available are tabulated.

| THERAPY | OBJECTIVE(S) | Limitation(s) |
|---|---|---|
| 1) GnRH Agonists[1] | Blocks estrogen secretion at pituitary axis level | By injection Accelerates osteoporosis Limited to preoperative use Side effects |
| 2) Cyclical Oral Progestagens[2,3] | Corrects estrogen progestagen ratio | Limited effectiveness Side effects |
| 3) Nonsteroidal Anti-inflammatory Agents | Local endometrial actions | Limited effectiveness Non-specific agent Side effects |

[1]Thomas et al., Br J Obstet Gynaecol, 98(11), 1155–1159 (1991).
[2]Fraser, Aust NZ J Obstet Gynaecol 30(4), 353–356 (1990).
[3]Bonduelle, Postgrad Med J, 67(791), 833–836 (1991).

When these therapies fail, surgery is usually indicated. Such surgery is usually either endometrial ablation or hysterectomy, but these procedures are associated with significant costs and side effects, (Thomas et al., supra.; Perino, *Acta Eur Ferti*, 21(6), 313–317 (1990)) some with a failure rate up to 20% (Fraser, supra.; Hellen, *Histopathology*, 22(4), 361–365 (1993)). A significant portion of the 500,00 hysterectomies performed annually in the USA are to treat dysfunctional uterine bleeding (Perino, Supra.)

SUMMARY OF THE INVENTION

A method of inhibiting dysfunctional uterine bleeding comprising administering to a human in need thereof an effective amount of a compound having the formula

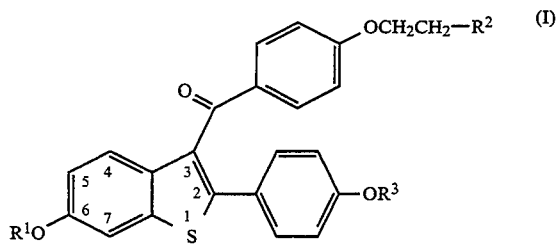

wherein $R^1$ and $R^3$ are independently hydrogen,

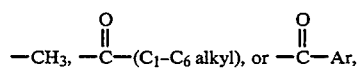

wherein Ar is optionally substituted phenyl;

$R^2$ is selected from the group consisting of pyrrolidine, hexamethylenemino, and piperidino; or a pharmaceutically acceptable salt of solvate thereof.

DETAILED DESCRIPTION OF THE INVENTION

The current invention concerns the discovery that compounds of formula I are useful for inhibiting dysfunctional uterine bleeding. The methods of treatment provided by this invention are practiced by administering to a female human a dose of a compound of formula 1, or a pharmaceutically acceptable salt or solvate thereof, that is effective to inhibit dysfunctional uterine bleeding.

The term "inhibiting dysfunctional uterine bleeding" includes reducing bleeding frequency and/or volume, whether it be within or outside of a normal cycle, or in the absence of of cycling, or in association with abnormal cycling, or inhibiting metrorrhagia. Also, the present method includes both medical therapeutic and/or prophylactic treatment, as appropriate.

Raloxifene, the hydrochloride salt of the compound of formula 1 wherein $R^1$ is hydrogen, $R^2$ is 1-piperidinyl, and $R^3$ is hydrogen, has been shown to bind to the estrogen receptor and was originally thought to be a molecule whose function and pharmacology was that of an anti-estrogen in that it blocked the ability of estrogen to activate uterine tissue and estrogen dependent breast cancers. Indeed, raloxifene does block the action of estrogen in some cells; however in other cell types, raloxifene activates the same genes as estrogen does and displays the same pharmacology, e.g., osteoporosis, hyperlipidemia. The unique profile which raloxifene displays and differs from that of estrogen is now thought to be due to the unique activation and/or suppression of various gene functions by the raloxifene-estrogen receptor complex as opposed to the activation and/or suppression of genes by the estrogen-estrogen receptor complex. Therefore, although raloxifene and estrogen utilize and compete for the same receptor, the pharmacological outcome from gene regulation of the two is not easily predicted and is unique to each.

Generally, the compound is formulated with common excipients, diluents or carriers, and compressed into tablets, or formulated as elixirs or solutions for convenient oral administration, or administered by the intramuscular or intravenous routes. The compounds can be administered transdermally or intravaginaly, and may be formulated as sustained release dosage forms and the like.

The compounds used in the methods of the current invention can be made according to established procedures, such as those detailed in U.S. Pat. Nos. 4,133,814, 4,418,068, and 4,380,635, all of which are incorporated by reference herein. In general, the process starts with a benzo[b]thiophene having a 6-hydroxyl group and a 2-(4-hydroxyphenyl) group. The hydroxyl groups of the starting compound are protected, the three position is acylated, and the product deprotected to form the formula I compounds. Examples of the preparation of such compounds are provided in the U.S. patents discussed above. The term "optionally substituted phenyl" includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferred salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, ethylene diamine and cyclohexylamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit dysfunctional uterine bleeding according to this invention will depend upon the the patient's physical characteristics, the route of administration, and related factors that will be evaluated by the attending physician. Generally, accepted and effective daily doses will be from about 0.1 to about 1000 mg/day, and more typically from about 30 to about 600 mg/day. Such dosages will be administered to a subject from once to about three times each day.

It is also advantageous to administer a compound by the oral route. For such purposes the following oral dosage forms are available.

FORMULATIONS

The term "active ingredient" relates to a compound of formula 1.

| Formulation 1: Gelatin Capsules | |
|---|---|
| Hard gelatin capsules are prepared using the following: | |
| Ingredient | Quantity (mg/capsule) |
| Active Ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of raloxifene capsule formulations include those shown below:

| Ingredient | Quantity (mg/capsule) |
|---|---|
| Formulation 2: Raloxifene Capsule | |
| Raloxifene | 1 |
| Starch, NF | 112 |
| Starch flowable powder | 225.3 |
| Silicone fluid 350 centistokes | 1.7 |
| Formulation 3: Raloxifene Capsule | |
| Raloxifene | 5 |
| Starch, NF | 108 |
| Starch flowable powder | 225.3 |
| Silicone fluid 350 centistokes | 1.7 |
| Formulation 4: Raloxifene Capsule | |
| Raloxifene | 10 |
| Starch, NF | 103 |
| Starch flowable powder | 225.3 |
| Silicone fluid 350 centistokes | 1.7 |
| Formulation 5: Raloxifene Capsule | |
| Raloxifene | 10 |
| Starch, NF | 150 |
| Starch flowable powder | 397 |
| Silicone fluid 350 centistokes | 3.0 |

The specific formulations above may be changed in compliance with the reasonable variations provided.

A tablet formulation comprising raloxifene is prepared using the ingredients below:

| Formulation 6: Tablets | |
|---|---|
| Ingredient | Quantity (mg/tablet) |
| Raloxifene | 0.1-1000 |
| Cellulose, microcrystalline | 0-650 |
| Silicon dioxide, fumed | 0-650 |
| Stearate acid | 0-15 |

The components are blended and compressed to form tablets.

Alternatively, tablets each containing 0.1-1000 mg of active ingredient are made up as follows:

| Formulation 7: Tablets | |
|---|---|
| Ingredient | Quantity (mg/tablet) |
| Active Ingredient | 0.1-1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1-1000 mg of medicament per 5 mL dose are made as follows:

| Formulation 8: suspensions | |
|---|---|
| Ingredient | Quantity (mg/5 ml) |
| Active Ingredient | 0.1-1000 mg |
| Sodium carboxymethyl cellulose | 50 mg |
| Syrup | 1.25 mg |
| Ben.oic arid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

TEST PROCEDURE

At least five women are selected for the clinical study. The women suffer from dysfunctional uterine bleeding. Because of the idiosyncratic and subjective nature of these symptoms, the study has a placebo control group, i.e., the women are divided into two groups, one of which receive the active agent of this invention and the other receive a placebo. The patients are evaluated as to the character of their dysfunctional uterine bleeding (blood loss, timing, etc.) prior to the study's initiation. Evaluations may also include uterine biopsy "estrogenicity scores" by histological assessment, and ultrasonic, radioimaging, NMR, or CAT scan evaluations of endometrial thickness. Women in the test group receive between 30-600 mg of the drug per day by the oral route. They continue this therapy for 3-12 months. Accurate records are kept as to the status of their dysfunctional uterine bleeding in both groups and at the end of the study these results are compared. The results are compared both between members of each group and also the results for each patient are compared to the symptoms reported by each patient before the study began.

Utility of the compounds of the invention is illustrated by the positive impact they have on the patients' dysfunctional uterine bleeding.

We claim:

1. A method of inhibiting dysfunctional uterine bleeding comprising administering to a human in need thereof an effective amount of a compound having the formula

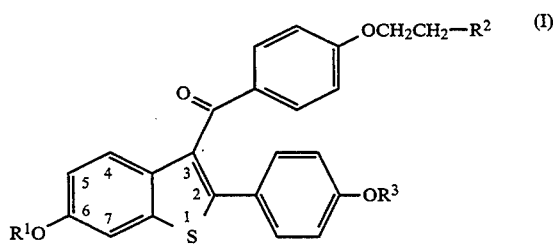

wherein $R^1$ and $R^3$ are independently hydrogen,

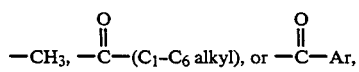

wherein Ar is optionally substituted phenyl;

$R^2$ is selected from the group consisting of pyrrolidine, hexamethylenemino, and piperidino; or a pharmaceutically acceptable salt of solvate thereof.
2. The method of claim 1 wherein said compound is the hydrochloride salt thereof.
3. The method of claim 1 wherein said compound is
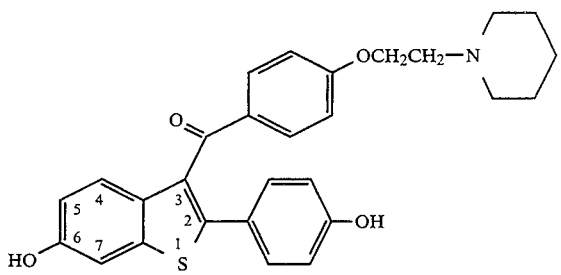
or its hydrochloride salt.
* * * * *